(12) United States Patent
Li et al.

(10) Patent No.: US 9,500,652 B2
(45) Date of Patent: Nov. 22, 2016

(54) MONOCLONAL ANTIBODY AGAINST DUCK TEMBUSU VIRUS, HYBRIDOMA CELL LINE AND APPLICATION THEREOF

(75) Inventors: Zejun Li, Shanghai (CN); Xuesong Li, Shanghai (CN)

(73) Assignee: Shanghai Veterinary Research Institute, CAAS, Shanghai (CN)

( * ) Notice: Subject to any disclaimer, the term of this patent is extended or adjusted under 35 U.S.C. 154(b) by 21 days.

(21) Appl. No.: 14/378,016

(22) PCT Filed: May 16, 2012

(86) PCT No.: PCT/CN2012/075553
§ 371 (c)(1),
(2), (4) Date: Dec. 3, 2014

(87) PCT Pub. No.: WO2013/117063
PCT Pub. Date: Aug. 15, 2013

(65) Prior Publication Data
US 2015/0086973 A1   Mar. 26, 2015

(30) Foreign Application Priority Data

Feb. 10, 2012 (CN) .......................... 2012 1 0030412

(51) Int. Cl.
*G01N 33/569* (2006.01)
*C07K 16/10* (2006.01)
*G01N 33/571* (2006.01)

(52) U.S. Cl.
CPC ...... *G01N 33/56983* (2013.01); *C07K 16/1081* (2013.01); *G01N 33/571* (2013.01); *C07K 2317/76* (2013.01); *G01N 2333/183* (2013.01)

(58) Field of Classification Search
None
See application file for complete search history.

(56) References Cited

U.S. PATENT DOCUMENTS

2015/0086973 A1*   3/2015   Li ...................... C07K 16/1081
435/5

OTHER PUBLICATIONS

Su et al. (PLoS One. Mar. 2011; 6 (3): e18106, pp. 1-10).*
Yan et al. (Virology. Jun. 2011; 417: 1-8).*
Deng et al. (PLoS One. Jan. 2011; 6 (1): e16059).*
Liu et al. (Journal of General Virology. Oct. 2012; 93: 2158-2170).*

* cited by examiner

*Primary Examiner* — Shanon A Foley
(74) *Attorney, Agent, or Firm* — Panitch Schwarze Belisario & Nadel LLP

(57) ABSTRACT

A monoclonal antibody against the Duck Tembusu virus and a hybridoma cell line secreting the monoclonal antibody, a reagent kit and method for detecting a Duck Tembusu virus antibody, and application of the monoclonal antibody in preparing products for diagnosing the Duck Tembusu virus disease. The monoclonal antibody may bind specifically to E protein of Duck Tembusu virus and has an activity of neutralizing Duck Tembusu virus.

8 Claims, 1 Drawing Sheet

MONOCLONAL ANTIBODY AGAINST DUCK TEMBUSU VIRUS, HYBRIDOMA CELL LINE AND APPLICATION THEREOF

CROSS REFERENCE TO RELATED APPLICATIONS

This is a national stage application based on PCT/CN2012/075553, filed on May 16, 2012, which claims priority to Chinese Patent Application No. CN 201210030412.0, filed on Feb. 10, 2012. This application claims the priority of these prior applications and incorporates their disclosures by reference in their entireties.

FIELD OF THE INVENTION

This invention relates to the field of immunochemical techniques, particularly relates to a monoclonal antibody against the Duck Tembusu virus, a hybridoma cell line and a blocking ELISA reagent kit for detecting a Duck Tembusu virus antibody using the monoclonal antibody.

BACKGROUND OF THE INVENTION

Duck Tembusu virus (DTMUV) is a flavivirus that may lead to reduction in egg laying, growth retardation and death of ducks. Since the spring of 2010, a new disease that leads to reduction in egg laying, growth retardation and death of ducks attacked successively in Shanghai, Jiangsu, Zhejiang, Anhui and other places. Studies have indicated that the pathogen causing this disease is Tembusu virus, which has pathogenicity for both egg-laying ducks and meat ducks. The sick ducks mainly have such symptoms as high fever, movement disorders, loss of appetite, reduced eggs laying and even stop, and even death if serious, with a mortality rate of up to 5%-10%. It is reported that the economic losses caused by DTMUV has exceeded RMB 5 billion yuan.

Currently, the molecular diagnostic methods for DTMUV have been established, but no reliable antibody detection methods are available.

SUMMARY OF THE INVENTION

The present invention is to resolve the technical problem that there is no reliable antibody detection method for DTMUV. It provides a monoclonal antibody against the Duck Tembusu virus, which can be used to detect DTMUV rapidly and sensitively.

In addition, the invention also provides a reagent kit and method for detecting a Duck Tembusu virus antibody using the said monoclonal antibody.

To solve the technical problems above, the present invention is conducted as follows:

In one aspect, the present invention provides a monoclonal antibody against Duck Tembusu virus.

Preferably, the monoclonal antibody is specially combined with E protein of Duck Tembusu virus, and having activity of neutralizing Duck Tembusu virus.

More preferably, the monoclonal antibody is secreted by hybridoma cell line 1F5 with accession number CCTCC NO: C201220, a vital sample of which was preserved in China Center for Type Culture Collection (CCTCC), No. 299, Ba Yi Road, Wuhan University, Wuchang, Wuhan, Hubei Province, China 430072, according to provisions of the Budapest Treaty on the International Recognition of the Deposit of Microorganisms for the Purposes of Patent Procedure on Jan. 17, 2012.

In another aspect, the present invention provides a hybridoma cell line that secretes a monoclonal antibody against Duck Tembusu virus, having the accession number CCTCC NO: C201220.

In another aspect, the invention provides a reagent kit for detecting a Duck Tembusu virus antibody, comprising the monoclonal antibody against Duck Tembusu virus.

Preferably, the reagent kit herein further comprises ELISA plates, Duck Tembusu virus antigen, antigen coating solution, blocking solution, antibody diluent, enzyme-labeled secondary antibody, color developing agent, stop solution, positive control serum, negative control serum, PBS-T washing solution (10×) and the reagent kit instructions. Among which, the positive control serum is SPF duck serum against Duck Tembusu virus and the negative control serum is the normal SPF duck serum; the enzyme-labeled secondary antibody is HRP-labeled anti-mouse secondary antibody.

In another aspect, the invention also provides a method for detecting a Duck Tembusu virus antibody, comprising:

coating an ELISA plate using purified Duck Tembusu virus antigen;

adding the monoclonal antibody against Duck Tembusu virus, enzyme-labeled secondary antibody, color developing agent in sequence when the test serum reacts with coated antigen;

reading the absorbance value $OD_{450nm}$ using a microplate reader, and calculating the inhibition rate of test serum according to the formula: inhibition rate (%)=(absorbance value of the negative control−absorbance value of test serum)/absorbance of negative control×100%, to obtain the test result.

The determination criteria of said test result are: If inhibition rate ≥18%, it is a positive result, if 13%<inhibition rate <18%, it is a suspicious result, and if inhibition rate ≤13%, it is a negative result.

Preferably, the optimal coating concentration of the antigen is 3 µg/hole; the optimal dilution factor of the test serum is 1:10; the optimal dilution factor of the monoclonal antibody is 1:20; the said enzyme-labeled secondary antibody is HRP-labeled anti-mouse secondary antibody and the optimal dilution factor is 1:5000.

The blocking ELISA reagent kit for detecting a Duck Tembusu virus antibody that is prepared by the monoclonal antibody have good specificity, and its sensitivity is significantly higher than that of agar diffusion test and virus neutralization test. It can be used to conduct rapid qualitative and quantitative tests of Duck Tembusu virus antibody, having a very good application prospect in the DTMUV disease diagnosis and antibody detection.

BRIEF DESCRIPTION OF THE DRAWINGS

The present invention will be further described below in details with reference to the accompanying drawings and the embodiments.

Figure 1:
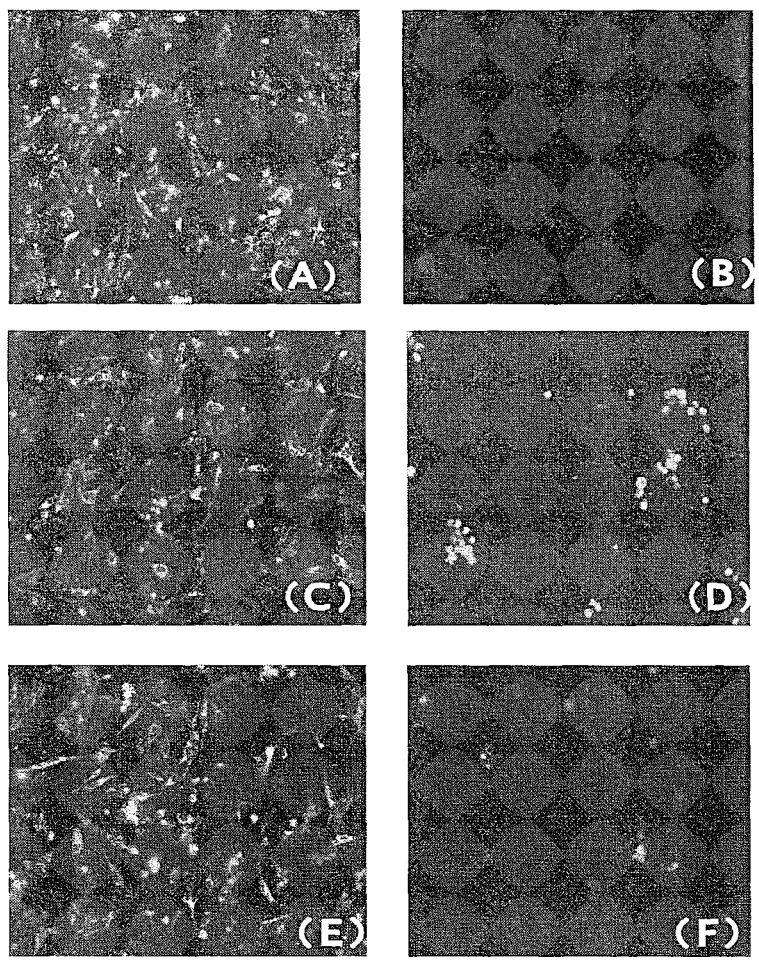
FIG. 1 is a graph illustrating immunofluorescence of specific reaction between the monoclonal antibody and DEF cells infected by DTMUV in Example 1 of the present invention.

The mouse hybridoma cell lines 1F5 secreting the monoclonal antibody against Duck Tembusu virus E protein was preserved in China Center for Type Culture Collection (for short CCTCC) on Jan. 17, 2012, with accession number CCTCC NO: C201220.

DETAILED DESCRIPTION OF THE INVENTION

In the following embodiments, experimental methods in which specific conditions are unspecified are typically carried out under general conditions, e.g. the method described in *Short Protocols in Molecular Biology* (Edited by Ausubel F. M., Kingston R. E., Seidman J. G. et al., Translated by MA, Xuejun, SHU, Yuelong. Beijing: Science Press, 2004)

In the present invention, in order to establish the antibody detection method against DTMUV, the BALB/c mice are immunized by a DTMUV strain (FX 2010), after screened through monoclonal antibody preparation technology, to obtain the hybridoma cell lines that can secrete a monoclonal antibody against Duck Tembusu virus stably. In a preferred embodiment of the present invention, the monoclonal antibody secreted by one hybridoma cell line can specifically bind with E protein of DTMUV, having the activity of neutralizing DTMUV. The monoclonal antibody is named 1F5. Then, coating a ELISA plate using purified Duck Tembusu virus; adding the monoclonal antibody 1F5, enzyme-labeled anti-mouse secondary antibody, color developing agent in sequence when the test serum reacts with coated antigen; reading the absorbance value $OD_{450nm}$ using a microplate reader, calculating the inhibition rate of test serum, and establishing a block ELISA method (B-ELISA) for detecting DTMUV antibody. The further preferable conditions show that the optimal concentration of coated antigen is 3 μg/hole, the optimal dilution factor of the test serum is 1:10, the optimal dilution factor of the monoclonal antibody 1F5 is 1:20, the optimal dilution factor of the enzyme-labeled anti-mouse secondary antibody is 1:5000. With higher sensitivity and specificity, the B-ELISA method for detecting DTMUV antibody will present a promising prospect in the diagnosis of DTMUV disease.

EXAMPLE 1

Preparation and Identification of a Monoclonal Antibody Against Duck Tembusu Virus 1 Materials and Methods 1.1 Viruses, Cells and Experimental Animals Duck Tembusu virus (DTMUV) Fengxian strain (FX2010 strain) was isolated and preserved by the laboratory; the duck embryo fibroblasts (DEF cells) and SP2/0 cells were provided by the laboratory; the clean grade BALB/c mice were purchased from Shanghai Laccas Experimental Animals Co., Ltd. The PCAGGS-DTMUV-E recombinant eukaryotic expression plasmids were constructed and preserved by our laboratory.

1.2 The Main Materials and Test Serum

DMEM was purchased from GBICO; 8-azaguanine, PEG1450, HAT, HT, Freund's complete adjuvant, Freund's incomplete adjuvant and HRP labeled goat-anti-mouse IgG were purchased from Sigma. DTMUV positive and negative sera, positive sera of avian influenza virus (AIV), Newcastle disease virus (NDV), reticuloendotheliosis virus (REV), type-I duck hepatitis virus (DHV-1), reovirus (RV) and avian leukemia virus (ALV) were preserved in our laboratory.

1.3 Preparation of Antigens

The DEF cells were infected by virus seed FX2010 at a dose of $10^{4.5}TCID50$; in 72 hours, cells having over 70% CPE were collected, after freeze-thaw for three times, inactivated for 24 h by 3% formaldehyde. After high-speed centrifuge 7500 rpm for 2 hours, the supernatant was fetched, and then centrifuged by ultracentrifugation 30000 rpm 5, to obtain the precipitation, to get the purified DTMUV. The protein concentration was determined and sub-packaged at −70° C., which were used as immunogen and coating antigen.

1.4 Preparation of DTMUV Monoclonal Antibody and its Identification 1.4.1 Immunization of Mice After the purified DTMUV antigen was added with equal amount of Freund's complete adjuvant for emulsification, the 6-8 week female BAB/c mice were injected with it subcutaneously from abdomen and back, 100 μg each mouse; After the purified DTMUV antigen was added with equal amount of Freund's incomplete adjuvant for emulsification, immunization was performed for the second time and third time every two weeks, with the dose same as the first time of immunization; two weeks after the third immunization, booster immunization was performed, and three days later, cells fusion started.

1.4.2 Establishment of Positive Hybridoma Cell Lines

The mouse peritoneal macrophages were prepared according to the conventional procedures, which were used as feeder cells. The spleen cells and myeloma cells (SP2/0) were fused under the reaction of fusion agent PEG1450 according to the ratio of 10:1. After screening of the positive myeloma cells by indirect ELISA, cloning was carried out according to limiting dilution analysis.

Results: through lymphocyte hybridoma technique and indirect ELISA, the hybridoma supernatants were detected, to obtain three hybridoma cell lines that can stably secrete anti-DTMUV monoclonal antibody, which were named 1F5, 7B5, 1E5 respectively.

1.4.3 Preparation of Monoclonal Antibody Ascitic Fluid 0.5 mL sterile paraffin oil was injected to abdominal cavity of mice, one week later, injected with $10^6$ hybridoma cells, 7-10 days later, when distension of the abdomen caused by ascitic fluid of mice, the ascitic fluid was drawn, and subpackaged for standby.

1.4.4 Identification of Monoclonal Antibodies through Indirect Immunofluorescence Assay (IFA)

The duck embryo fibroblasts (DEF cells) were prepared and cultured in 6-well plates. When the cell monolayers grown, DEF cells were infected by DTMUV, meanwhile, negative control holes were set. 24 hours after infection, the supernatant was discarded, and the cells were fixed with 4% paraformaldehyde. After washed three times by PBST, hybridoma cultural supernatant was added, and incubated for 1 h at 37° C., washed three times using PBST, added with FITC-goat anti-mouse IgG antibody, continued to incubate for 1 hour at 37° C., washed three times using PBST, and finally observed under a fluorescence microscope. Those with green fluorescence were judged as positive, and those without fluorescence were judged as negative.

Results: DEF cells were infected by DTMUV. IFA was performed using three strains of monoclonal antibodies and the uninfected DEF cells were set as blank control (MOCK). The test results showed that, three strains of monoclonal antibodies 1F5, 7B5, 1E5 all could produce specific green fluorescence (as shown in FIG. 1), indicating that all three strains can specifically bind with DTMUV protein. In FIG. 1, (A): MAb 1F5; (B): MOCK-1F5; (C): MAb 7B5; (D): MOCK-7B5; (E): MAb 1E5; (F): MOCK-1E5.

EXAMPLE 2

Identification of a Monoclonal Antibody Against Duck Tembusu Virus E Protein 1. Identification of a Monoclonal Antibody Again Duck Tembusu Virus E Protein 293 cells were cultured in 6-well plates, when the cell monolayers grown, 293 cells were transfected by eukaryotic expression recombinant plasmid pCAGGS-DTMUV-E, meanwhile, negative control holes were set. 24 hours after transfection, the supernatant was discarded, and the cells were fixed with 4% paraformaldehyde. After washed once by PBST, hybridoma cultural supernatant was added, and incubated for 1 h at 37° C., washed three times using PBST, added with FITC-goat anti-mouse IgG antibody, continued to incubate for 1 hour at 37° C., washed three times using PBST, and finally observed under a fluorescence microscope. Those with green fluorescence were judged as positive, and those without fluorescence were judged as negative.

Figure 2:
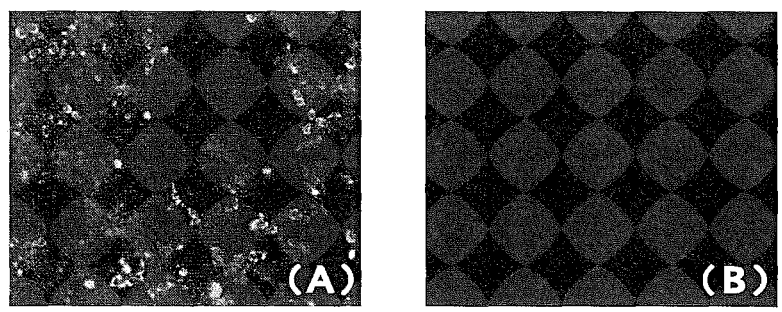
FIG. 2 is a graph illustrating immunofluorescence of specific binding between 1F5 monoclonal antibody and PCAGGs-DTMUV-E transfected 293T cells in Example 2 of the present invention.

Results: Through IFA detection of 293 T cells transfected by PCAGGS-DTMUV-E eukaryotic plasmids, the controlled empty plasmid pCAGGS-transfected 293T cells had no specific fluorescence; while specific green fluorescence appeared in 1F5 (as shown in FIG. 2), but no green fluorescence in another two strains of monoclonal antibodies, which further confirmed that mAb 1F5 was the monoclonal antibody of anti-DTMUV E protein. In FIG. 2, (A): PCAGGS-DTMUV-E-transfected 293T cells; (B): pCAGGS-transfected 293T cells.

The stain of hybridoma cell line that secreted monoclonal antibody against Duck Tembusu virus E protein, i.e. mouse hybridoma cell line 1F5 of anti-DTMUV E protein, was preserved in China Center For Type Culture Collection (CCTCC) on Jan. 17, 2012, with accession No. CCTCC NO: C201220.

2. Determination of Neutralizing Activity of Monoclonal Antibodies

The virus neutralization test was performed using fixed virus antibody dilution method, to detect the neutralizing activity of monoclonal antibodies. The hybridoma cell culture supernatant and ascites were diluted by two-fold series after inactivated 30 min at 56° C., and mixed with equal volume of DTMUV (FXV2010 strain) containing 100ELD$_{50}$ at 37° C. for 1 h, and then inoculated to 7-day-old SPF chicken embryo; Meanwhile, the DTMUV positive serum, SP2/0 cell culture supernatant were set as the positive control and negative control. The highest dilution factor of antibody that can inhibit the virus replication by 50% was determined as the neutralizing antibody titer.

The neutralization test showed that, 1F5 monoclonal antibody had the DTMUV neutralizing activity. The neutralizing antibody titer of 1F5 monoclonal antibody cell culture supernatant was 1:64 and the neutralizing antibody titer of ascites was 1:512.

EXAMPLE 3

Establishment of Block ELISA Method (Blockinge ELISA, B-ELISA) for Detecting DTMUV Antibody 1. Preparation of Negative Serum 6-week-old SPF ducks were used, to collect blood from heart, and then the serum was separated, and dispensed in 0.2 mLEp tubes, kept at −20° C. for future use.

2. Preparation of Positive Serum 6-week-old SPF ducks were infected nasally by $10^{3.5}$ELD$_{50}$DTMUV FX2010 isolates. 3 weeks later, blood was collected from heart, and then the serum was separated, and dispensed in 0.2 mLEp tubes, kept at −20° C. for future use.

3. The Procedures for DTMUV Antibody Block ELISA

The purified DTMUV was diluted to 0.03 mg/mL using 0.05 mol/L carbonate buffer solution (pH 9.6), coated 96-well microtiter plate, 100 μL each well, overnight at 4° C., and closed for 1 h at 37° C. using PBS (0.01 mol/L, pH 7.4) solution containing 5% skim milk powder, and then washed three times with PBS (PBST) containing 0.5 mL/L TWEEN 20. The DTMUV-positive and negative sera diluted by PBS were added to closed microtiter plates separately, sealed with parafilm, mixed for 1 h at 37° C., and then washed 3 times using PBST. 1F5 monoclonal antibody was diluted 1:20, added with 100 μL each well, mixed for 1 h at 37° C.; added with the 5000-fold diluted HRP-anti-mouse IgG 100 μL; and then added with 100 μL of TMB color developing agent, developing for 10 min at darkness, and finally added with 50 μL of stop solution (2 mol/L of H$_2$SO4) to stop the reaction, and measure the OD450 nm values.

4. Determination of Critical Values

B-ELISA detection was performed for 350 portions of duck negative sera, and the detection results were statistically analyzed, to calculate the average inhibition rate of negative samples and the standard deviation (SD). The critical values were calculated separately according to the formula: critical value=average inhibition rate of negative samples+3×standard deviation (SD).

Results: The average inhibition rate of 350 portions of duck negative sera was 0.95% and the standard deviation was 5.79%. Calculated according to the formula: critical value=average inhibition rate of negative samples+3×standard deviation (SD), the critical value was 18%. When the inhibition rate ≥18%, the DTMUV antibody was positive for the serum samples; when 13%<inhibition rate <18%, the serum was suspicious; when inhibition rate ≤13%, the DTMUV antibody was negative.

5. Specificity Test

The positive sera of H5N1 and H9N2 subtype avian influenza virus (AIV), Newcastle disease virus (NDV), reticuloendotheliosis virus (REV), type-I duck hepatitis virus (DHV-1), reovirus (RV) and avian leukosis virus (ALV) were detected by the established B-ELISA, to validate cross-reactivity of the kit in the invention on positive sera of other viruses.

Results showed that, after detection by B-ELISA, only DTMUV positive serum presented positive, with the inhibition rate of 69.13%, higher than 18%; the positive serum of other viruses presented negative (as shown in Table 1), indicating that the method and kits herein have good specificity.

TABLE 1

| B-ELISA specificity test | | | | | | |
|---|---|---|---|---|---|---|
| | Positive Sera | | | | | |
| | AIV | NDV | DHV-1 | RV | ALV | DTMUV |
| Inhibition Rate (PI) | 1.20% | 0.50% | 0.13% | −0.20% | 2.30% | 69.13% |

6. Sensitivity Test

The known DTMUV positive serum was detected by the established B-ELISA, agar diffusion test (AGP), and serum neutralization test (SNT) respectively, to compare the sensitivity difference between them.

Results showed that, the sensitivity of B-ELISA was significantly higher than that of AGP and SNT (as shown in Table 2).

TABLE 2

Comparison of sensitivity between B-ELISA, AGP and SNT

| | Antibody dilution | | | | | | | |
|---|---|---|---|---|---|---|---|---|
| | 2 | 4 | 8 | 16 | 32 | 64 | 128 | 256 |
| B-ELISA | + (76.71%) | + (70.90%) | + (64.36%) | + (54.37%) | + (40.93%) | + (29.32%) | ± (15.65%) | − (4.05) |
| AGP | + | − | − | − | − | − | − | − |
| SNT | + | + | + | + | + | − | − | − |

Note:
+ represented positive DTMUV antibody,
± represented suspicious DTMUV antibody,
− represented negative DTMUV antibody.

7. Repeatability Test (1) Within-run repeatability test: Different samples were detected using the same batch of coated microtiter plates. One positive sample, one negative sample, 6 holes repeated for each sample, and B-ELISA test was performed, to calculate the coefficient of variation of inhibition rate for the same sample, to test the within-run repeatability;

(2) Between-run repeatability test: One positive sample and one negative sample were tested repeatedly using different batches of coated microtiter plates. B-ELISA test was performed, to calculate the coefficient of variation of inhibition rate for the same sample, to test the between-run repeatability.

Results: The statistical analysis of the inhibition rates of the within-run repeatability test and between-run repeatability test of the same batch and different batches of B-ELISA showed that, the coefficient of variation was less than 10%, indicating that the kits had good repeatability (as shown in Table 3 and Table 4).

TABLE 3

Within-run repeatability test

| | Parallel Holes | | | | | | CV |
|---|---|---|---|---|---|---|---|
| Sample | 1 | 2 | 3 | 4 | 5 | 6 | CV % |
| Positive | 73.18 | 69.63 | 68.58 | 71.26 | 69.39 | 73.81 | 4.16% |
| Negative | 4.21 | 4.42 | 3.81 | 4.75 | 4.63 | 4.39 | 6.96% |

TABLE 4

Between-run repeatability test

| | Parallel Holes | | | | | | CV |
|---|---|---|---|---|---|---|---|
| Sample | 1 | 2 | 3 | 4 | 5 | 6 | CV % |
| Positive | 68.17 | 71.32 | 77.43 | 76.96 | 64.82 | 76.21 | 7.22% |
| Negative | 4.87 | 5.03 | 5.22 | 3.99 | 4.86 | 5.01 | 8.94% |

EXAMPLE 4

Composition of DTMUV Antibody Block ELISA (B-ELISA) Kit and its Application

1. The Composition of Kit

The kit was assembled with the items listed in Table 5. After assembly, keep them in the appropriate conditions.

TABLE 5

DTMUV antibody block ELISA test kit

| No. | Item | Qty | Remark |
|---|---|---|---|
| 1 | Removable ELISA plate to be coated | 1 | Size 8 × 12, preserved at 4° C. |
| 2 | Coated antigen | 1 tube | 100 µL/tube, preserved at −20° C. |
| 3 | Coating buffer (1×) | 1 bottle | 10 mL/bottle, preserved at 4° C. |
| 4 | Blocking solution | 1 bottle | 20 mL/bottle, preserved at 4° C. |
| 5 | Positive control serum | 1 tube | 50 µL/tube, preserved at −20° C. |
| 6 | Negative control serum | 1 tube | 50 µL/tube, preserved at −20° C. |
| 7 | Monoclonal antibody | 1 tube | 100 µL/tube, preserved at −20° C. |
| 8 | HRP-anti-mouse IgG (5000×) | 1 tube | 5 µL/tube, preserved at −20° C. |
| 9 | Antibody dilution (1×) | 1 bottle | 10 mL/tube, preserved at 4° C. |
| 10 | TMB color developing solution | 1 bottle | 10 mL/bottle, preserved at 4° C. |
| 11 | Stop solution | 1 bottle | 10 mL/bottle, preserved at 4° C. |
| 12 | PBS-T scrubbing solution (10×) | 1 bottle | 50 mL/bottle, preserved at 4° C. |
| 13 | Kit instructions | 1 | |

2. Instructions for the Use of the Kit:

1) Procedures:

A. coating: The removable ELISA plates were coated with coating antigen one day before the detection. The coating antigen of the above reagent was mixed in the coating buffer evenly, 100 µL/well, 4° C. overnight, on the next day, taken out and washed three times using 1×PBS-T scrubbing solution, 3 min each time;

B. Block: 20 µL/well of blocking buffer, 1 h at 37° C., washed three times using 1× scrubbing solution, 3 min each time;

C. The test serum, positive and negative control sera were diluted 10-fold with an antibody diluent for standby, and added to ELISA plates, 100 µL per well, incubated for 1 hour at 37° C.; washed three times using 1× scrubbing solution, 3 min each time, procedures same as above;

D. Dilute monoclonal antibody using 20× antibody diluent, 100 μL monoclonal antibody per well, incubated for 1 hour at 37° C.; washed three times;

E. Add 100 μL of HRP-anti-mouse IgG diluted to 1× by antibody diluent to each well, 37° C. for 1 h, and washed three times;

F. Add TMB chromogenic substrate solution 100 μL to each well, developing 10 min in the darkness at room temperature;

G. Add 50 uL of stop solution to each well, read the absorbance value $OD_{450nm}$ from microplate reader, calculate the inhibition rate. The inhibition rate (%)=(absorbance of negative control−absorbance of test serum)/absorbance of negative control×100%.

2) Judgment and Analysis of Test Results

When the inhibition rate of positive serum was greater than 50%, the experimental results were reliable, judge them according to the following criteria:

When the inhibition rate of serum samples was greater than or equal to 18%, the sample can be judged positive DTMUV antibody;

When the inhibition rate of serum samples was less than or equal to 13%, the sample can be judged negative DTMUV antibody;

When 13%<inhibition rate of serum samples <18%, the sample can be judged suspicious, and still suspicious after repeated test, it can be judged negative.

3. Application of the Kit 130 duck serum samples from different places were determined using the established B-ELISA. Results showed that, among the 130 duck serum samples, 32 samples were positive, 98 samples were negative, with the positive rate of 24.62%.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A monoclonal antibody that specifically binds to an E protein of Duck Tembusu virus, wherein the monoclonal antibody is produced by a hybridoma cell line having an accession number CCTCC NO: C201220.

2. A hybridoma cell line that secretes a monoclonal antibody against Duck Tembusu virus, having an accession number CCTCC NO: C201220.

3. A reagent kit for detecting a Duck Tembusu virus antibody, comprising the monoclonal antibody of claim 1.

4. The reagent kit according to claim 3, wherein the reagent kit further comprises an ELISA plate, a Duck Tembusu virus antigen, an enzyme-labeled secondary antibody, a color developing agent, a positive control serum and a negative control serum, wherein the Duck Tembusu virus antigen is a Duck Tembusu virus E protein or inactivated Duck Tembusu virus.

5. The reagent kit according to claim 4, wherein the positive control serum is an SPF duck serum against Duck Tembusu virus and the negative control serum is a normal SPF duck serum.

6. A method for detecting a Duck Tembusu virus antibody in a sample, comprising:
(i) coating a well of an ELISA plate with a purified Duck Tembusu virus antigen;
(ii) contacting the well with the sample, adding to the well (a) the monoclonal antibody of claim 1, (b) an enzyme-labeled secondary antibody, and (c) a color developing agent in the sequence of (a) to (c); and
(iii) detecting binding between the Duck Tembusu virus antigen and the antibody.

7. The method according to claim 6, wherein step (iii) comprises (a) reading the absorbance value $OD_{450nm}$ using a microplate reader and (b) calculating an inhibition rate of the test serum sample according to the formula:

inhibition rate (%)=[(absorbance value of the negative control−absorbance value of test serum)/ absorbance value of negative control]×100%, wherein an inhibition rate ≥18% indicates a positive result, an inhibition rate >13% and <18% indicates a suspicious result, and an inhibition rate ≤13% indicates a negative result.

8. A method for diagnosing Duck Tembusu virus disease in a subject, comprising:
obtaining a test serum sample from the subject; and
detecting a Duck Tembusu virus antibody in the test serum using the method of claim 6.

* * * * *